United States Patent [19]
Baker

[11] Patent Number: 6,083,223
[45] Date of Patent: Jul. 4, 2000

[54] METHODS AND APPARATUS FOR WELDING BLOOD VESSELS

[76] Inventor: James A. Baker, 4292-P Wilkie Way, Palo Alto, Calif. 94306

[21] Appl. No.: 09/191,413

[22] Filed: Nov. 12, 1998

Related U.S. Application Data

[63] Continuation-in-part of application No. 08/920,291, Aug. 28, 1997, Pat. No. 5,957,920
[60] Provisional application No. 60/065,366, Nov. 12, 1997.

[51] Int. Cl.⁷ ...................................................... A61B 18/18
[52] U.S. Cl. ................................................. 606/52; 606/49
[58] Field of Search ................................ 606/41, 49, 50, 606/51, 52, 42

[56] References Cited

U.S. PATENT DOCUMENTS

| | | | |
|---|---|---|---|
| 4,655,216 | 4/1987 | Tischer | 606/51 |
| 5,151,102 | 9/1992 | Kamiyama et al. | |
| 5,269,780 | 12/1993 | Roos | |
| 5,290,287 | 3/1994 | Boebel et al. | |
| 5,403,312 | 4/1995 | Yates et al. | |
| 5,443,463 | 8/1995 | Stern et al. | 606/51 |
| 5,445,638 | 8/1995 | Rydell et al. | 606/51 |
| 5,458,598 | 10/1995 | Feinberg et al. | 606/52 |
| 5,573,535 | 11/1996 | Viklund | 606/51 |
| 5,702,390 | 12/1997 | Austin et al. | 606/48 |
| 5,735,849 | 4/1998 | Baden et al. | 606/51 |
| 5,833,690 | 11/1998 | Yates et al. | |
| 5,891,141 | 4/1999 | Rydell | 606/45 |

*Primary Examiner*—Michael Peffley
*Attorney, Agent, or Firm*—Fish & Neave; Nicola A. Pisano

[57] ABSTRACT

Methods and apparatus are provided for welding or sealing blood vessels or tissue by capturing and stretching the tissue to alter its impedance characteristics prior to application of RF energy. The apparatus includes a working end including a perimeter jaw structure for engaging opposing ends of a section of a targeted blood vessel, and an interior jaw arm that passes through the plane of engagement and stretches the portion of the vessel intermediate the opposing ends, and two or more electrodes for applying RF current. The working end also may include one or more sensors providing signals to a power controller that modulates application of RF energy to the tissue.

40 Claims, 7 Drawing Sheets

METHODS AND APPARATUS FOR WELDING BLOOD VESSELS

REFERENCE TO RELATED APPLICATIONS

This application claims priority from U.S. provisional application Ser. No. 60/065,366, filed Nov. 12, 1997, which is a continuation-in-part application of U.S. patent application Ser. No. 08/920,291, filed Aug. 28, 1997, now U.S. Pat. No. 5,957,920.

FIELD OF THE INVENTION

This invention relates to methods and apparatus for sealing and welding blood vessels and vascularized tissue masses using RF energy. More particularly, this invention relates to manipulating tissue to control RF energy delivery by altering tissue impedance.

BACKGROUND OF THE INVENTION

In both open and endoscopic surgeries, it often is necessary to seal, weld or cauterize blood vessels or other vascularized tissues. For example, in subfacial endoscopic perforator surgery (SEPS), a perforator vessel in a patient's leg is sealed or welded closed to alleviate the effects of a venous ulceration. In a typical SEPS procedure, the surgeon uses a mechanically deformable clip to pinch off the perforator vessel. Because a single clip may not seal the vessel reliably, multiple clips typically are used to assure an effective seal. It would be preferable to seal a vessel without leaving such metal clips implanted in the patient's body.

Ultrasound and radiofrequency devices have been developed for sealing blood vessels but such devices often will not create a secure seal, particularly when used on larger diameter blood vessels. Previously known commercially available ultrasound devices suffer from the disadvantage of being slow to deliver sufficient energy to seal a blood vessel. In addition, ultrasound devices generally are capable of thermally treating only a narrow band across a target blood vessel (due to the focused nature of the ultrasound beam), and thus may not provide a reliable seal. To improve the chances of a permanent seal, surgeons often apply ultrasound energy at multiple locations along a blood vessel, a practice that is inconvenient and time-consuming.

Previously known commercially available RF instruments for sealing blood vessels deliver energy more quickly than ultrasound devices. A typical previously known RF bi-polar grasper, suitable for such procedures, is described with respect to FIGS. 1A and 1B. Such an instrument may be used to seal a blood vessel by squeezing the vessel between the opposing jaw faces of the grasper while applying an RF current (FIG. 1B). Each jaw face comprises a conductive electrode (first electrode 2A and second electrode 2B) and when operated in a bi-polar mode, RF current flows directly "across" vessel 3 in the direction indicated by the arrow in FIG. 1B between first electrode 2A and second electrode 2B.

Figure 1A:
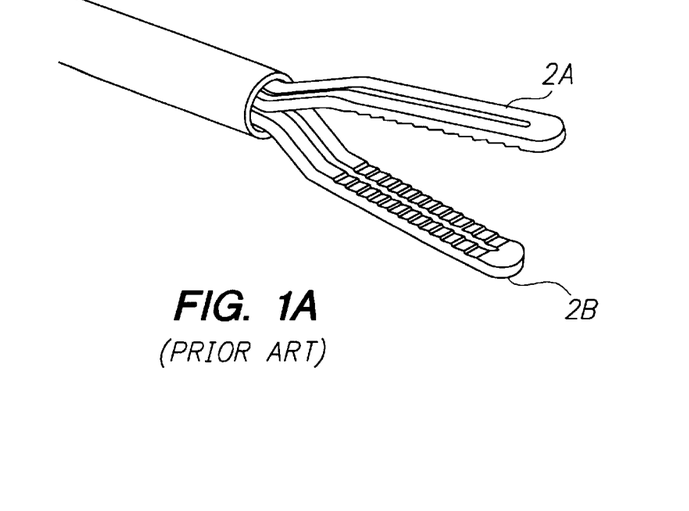
FIGS. 1A–1B are perspective views depicting the distal end of a jaw structure of a previously known radiofrequency device and its use in cauterizing a blood vessel.
Figure 1B:
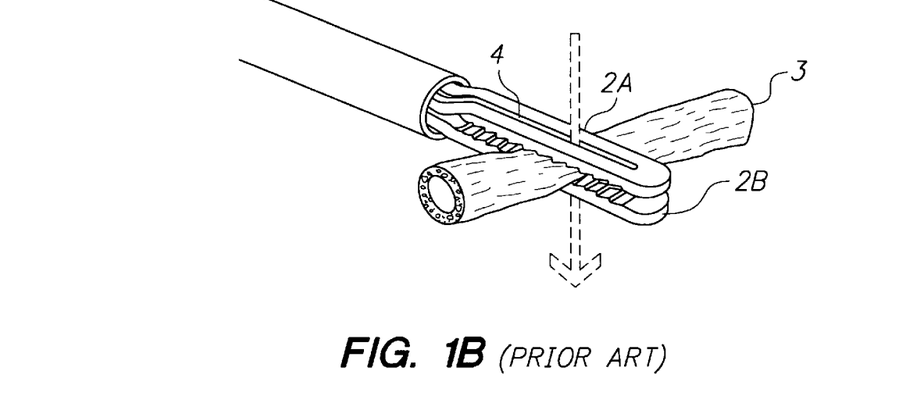

The integrity of the sealing effect achieved with the device of FIGS. 1A and 1B is greatly influenced by the conductive characteristics of the target tissue. For example, the impedance of the tissue of the vessel walls and endothelium changes continuously during the application of RF energy. Impedance typically increases quickly during energy application until the bi-polar RF energy flow is impeded or restricted altogether. Often this will occur before the vessel walls around the lumen are fused in a uniform manner. Effective sealing of the vessel therefore depends on providing an appropriate energy delivery profile (i.e., energy level delivered to the tissue over an appropriate time interval) to cause fusion of molecules within a targeted region, with little or no charring or carbonization.

Because tissue impedance is an uncontrolled variable when using previously known methods and apparatus, the effectiveness of such previously known tissue welding apparatus and methods can be highly variable. It is for this reason that previously known commercially available RF devices have not provided reliable sealing for large blood vessels.

It would therefore be desirable to provide methods and apparatus, preferably utilizing RF energy, that control the effects of tissue impedance to provide an effective energy delivery profile in tissue targeted for welding.

It further would be desirable to provide methods and apparatus that control the effects of tissue impedance to reduce charring of tissue and the creation of smoke in an endoscopic workspace.

SUMMARY OF THE INVENTION

In view of the foregoing, it is an object of this invention to provide methods and apparatus, preferably utilizing RF energy, that control the effects of tissue impedance to provide an effective energy delivery profile in tissue targeted for welding.

It is a further object of the present invention to provide methods and apparatus that control the effects of tissue impedance to reduce charring of tissue and the creation of smoke in an endoscopic workspace.

These and other objects of the present invention are accomplished by providing apparatus and methods for applying RF energy to tissue wherein the tissue subjected to welding or sealing is manipulated to alter its impedance characteristics prior to the application of RF energy.

In a preferred embodiment, the apparatus comprises a jaw subassembly that engages and extends a portion of targeted tissue to provide an elongated section having substantially uniform impedance. More particularly, the apparatus includes an elongated shaft carrying a distal working end having a jaw structure configured for grasping and manipulating a target section of a blood vessel or vascularized tissue.

The jaw structure includes first and second jaw members having opposing perimeter jaw faces for grasping opposing ends of a targeted longitudinal section of a vessel. An extension member operatively associated with the first and second jaw members then extends (or stretches under tension) the section of the vessel intermediate the ends. The right and left sides of the jaw structure carry conductive electrodes, preferably operable in a bi-polar mode, so that an RF current flows between the electrodes and along the length of the section of vessel that has been extended or stretched.

In an alternative embodiment, the jaw assembly further includes one or more sensors for measuring physiologic parameters of the portion of the vessel targeted for welding, such as temperature or impedance, and for controlling the application of RF energy responsive to the measured parameters.

Methods of using the foregoing apparatus are also provided. A first method of the invention relates to altering certain impedance characteristics of tissue targeted for welding to enhance the RF delivery profile. Specifically, a length of the tissue or blood vessel is extended to reduce its extracellular fluid (ECF) content level. This in turn causes the ECF level to become more uniformly distributed throughout the extended section of tissue, and increases the impedance of the target tissue to RF current. The increased impedance of the extended section therefore forms a "fuse" or "fuse point" that facilitates welding when an RF current is passed longitudinally through the tissue.

In an alternative method, the RF current applied to the extended section of tissue is controlled in response to a measured physiologic parameter, such as temperature or impedance of the extended section of tissue, or power delivered to the tissue to reduce charring and smoke generation.

BRIEF DESCRIPTION OF THE DRAWINGS

Additional objects and advantages of the invention will be apparent from the following description, the accompanying drawings and the appended claims, in which:

DETAILED DESCRIPTION OF THE INVENTION

The present invention provides methods and apparatus for sealing or welding a blood vessel by extending or stretching a section of the blood vessel prior to application of RF energy. As used herein, the term "blood vessel" is defined to include any artery or vein of any size, and further includes any vascularized tissue mass.

As is known in the art of electrosurgical instruments, the application of high frequency alternating current causes ionic agitation and friction in a targeted vessel or tissue as ions follow the changes in direction of the alternating current. Such ionic agitation or frictional heating thus does not result from direct tissue contact with a resistive electrode. Energy delivered to a tissue mass may be computed using the formula: $I=E/R$ where I is the intensity of the current in amperes, E is the energy potential measured in volts and R is the tissue resistance measured in ohms.

Current density (i.e., the level of current intensity) can be used as a gauge of energy delivery, and varies as a function of the impedance of the targeted tissue mass. The amount of heat generated within a targeted tissue is known to be influenced by several factors, including (i) the RF current intensity, (ii) the RF current frequency, (iii) the instantaneous impedance level of the targeted tissue (which varies during a treatment cycle), (v) heat dissipation from the targeted tissue; (vi) the duration of RF energy delivery, and (vii) the distance traveled by the RF current through the targeted tissue between the conductive electrodes.

Applicants have discovered that by extending or stretching a targeted tissue a reproducible amount, it is possible to influence the amount of extracellular fluid (ECF) present in the tissue, and thus alter the impedance of the tissue. In particular, applicants have determined that by manipulating the targeted tissue, it is possible to create a "fuse" or "fuse point" in the tissue that is preferentially heated RF energy is applied to the tissue.

Applicants further have determined that the creation of a "fuse point" offers several advantages over previously known methods and apparatus for RF delivery, including: (1) achieving greater levels of thermal effect at lower levels of power (current intensity); (2) preferential heating of the tissue in the vicinity of the fuse point, thereby speeding up the tissue welding process; (3) the formation of a more lengthy and effective weld in the fuse point section of the tissue compared to previously known devices; (4) more uniform thickness and impedance within the targeted tissue, thereby providing for more uniform heating in the vicinity of the fuse point; and (5) reduced thermal trauma outside the vicinity of the fuse point. In addition, it is expected that the more uniform heating of tissue provided by the methods and apparatus of the present invention will substantially reduce smoke generation and localized tissue charring.

Figure 2:
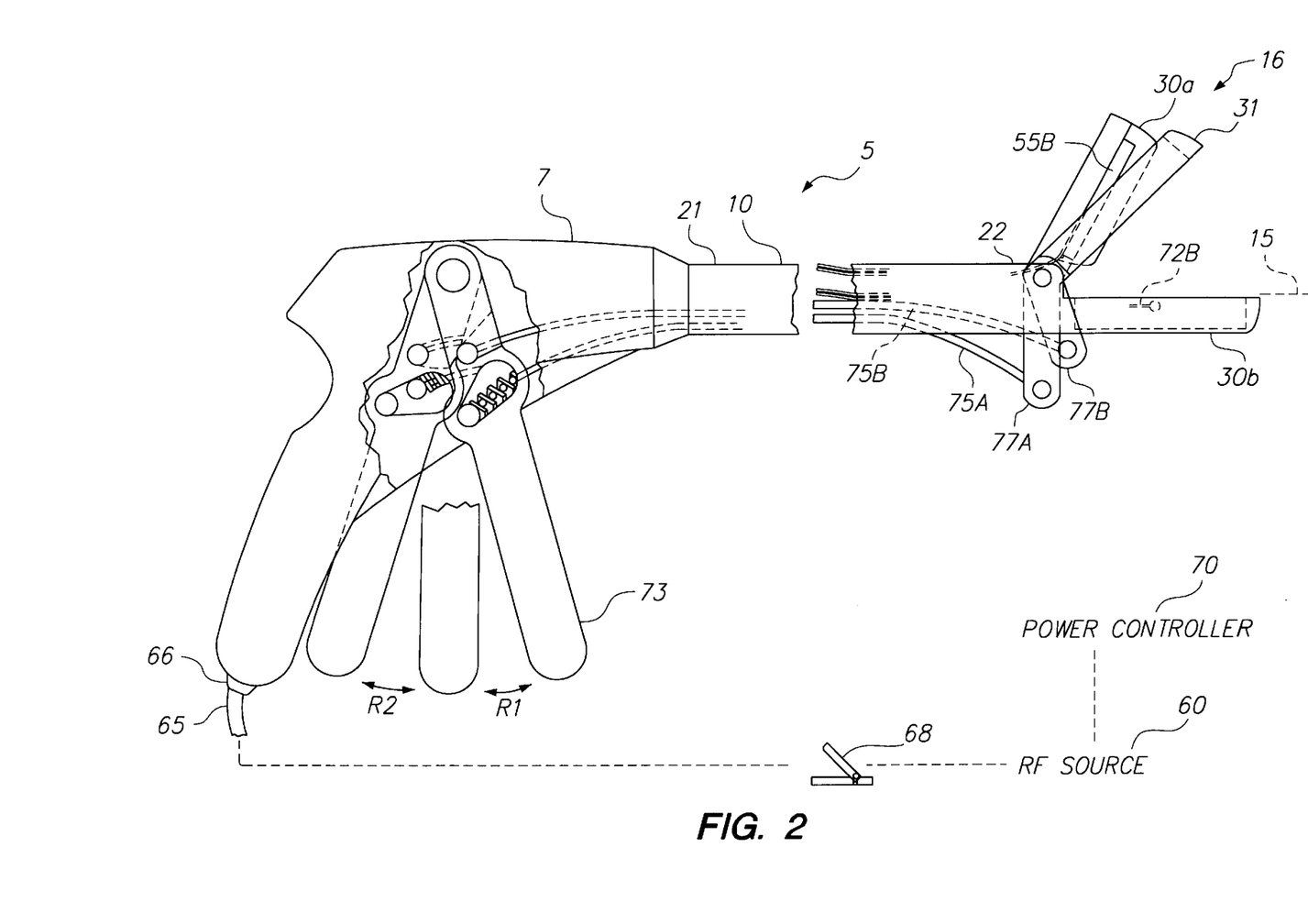
FIG. 2 is an elevational view of a first embodiment of a radiofrequency (RF) device constructed in accordance with the principles of the present invention.

Referring now to FIG. 2, a first embodiment of device 5 constructed in accordance with the principles of the present invention is described. Device 5 is adapted for use in open or endoscopic procedures and comprises plastic handle assembly 7 coupled to elongated shaft 10 extending along axis 15 and carrying distal working end 16. Shaft 10 has proximal end 21 and distal end 22, and illustratively has a cylindrical cross-section. Handle assembly 7 and shaft 10 preferably comprise any of a number of suitable materials, such as metal or plastic. In an embodiment of device 5 suitable for performing a SEPS procedure, shaft 10 preferably has an outer diameter in a range from 5 mm. to 10 mm., e.g., to enable use of the device with previously known endoscopic trocar sleeves.

Figure 3A:
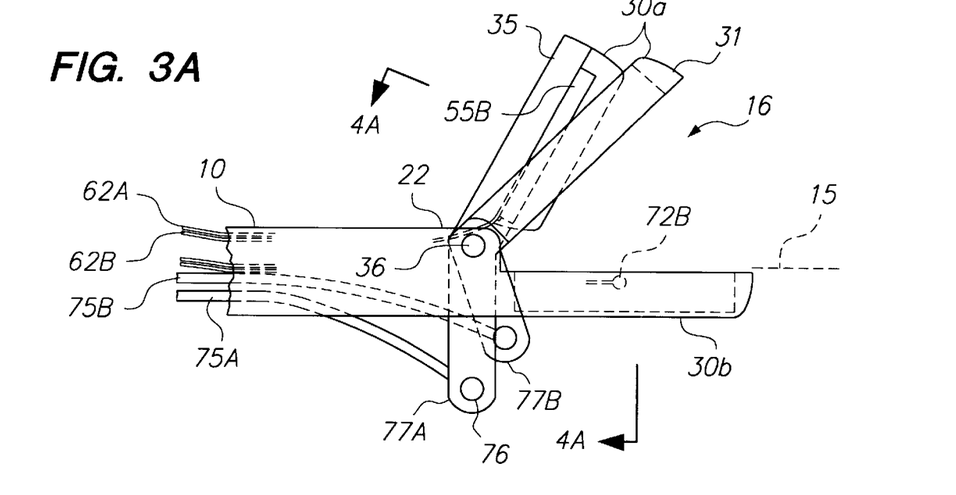
FIGS. 3A–3C are enlarged elevational views of the working end of the device of FIG. 2 depicting with the jaw assembly during various stages of operation.
Figure 3B:
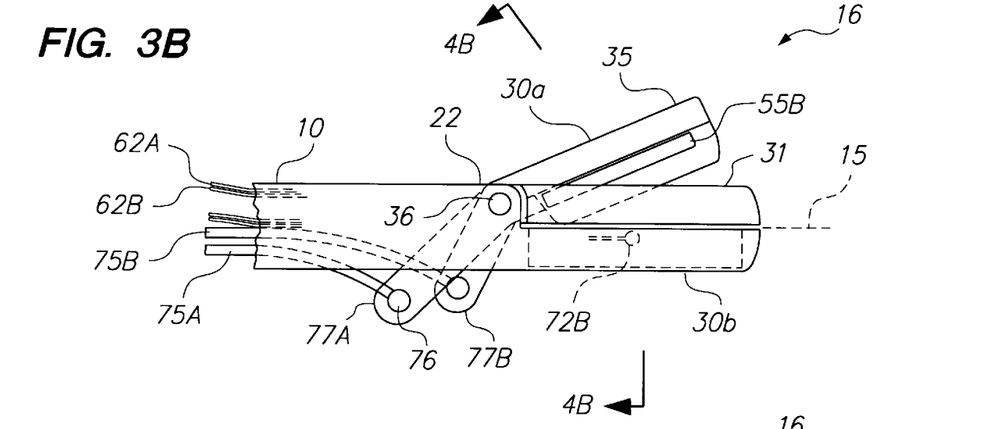
Figure 3C:
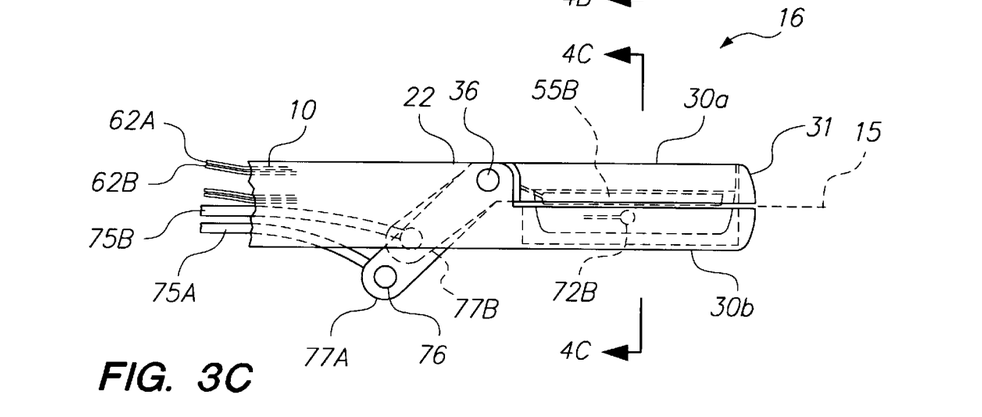

Referring now also to FIGS. 3A–3C, working end 16 comprises a jaw structure carried by shaft 10 that includes upper jaw assembly 30a and lower jaw arm 30b disposed in opposing relation to upper jaw assembly 30a. Upper jaw assembly 30a comprises independently moveable interior jaw arm 35 disposed in slot 41 of perimeter jaw 31. Interior jaw arm 35 is independently moveable with respect to both perimeter jaw 31 and lower jaw arm 30b. Upper jaw assembly 30a and lower jaw arm 30b preferably comprise a nonconductive material such as plastic, or may comprise a metal or metal alloy coated with a suitable electrically insulative material. Upper jaw assembly 30a preferably includes at least one RF electrode, described in greater detail hereinbelow.

Figure 4A:
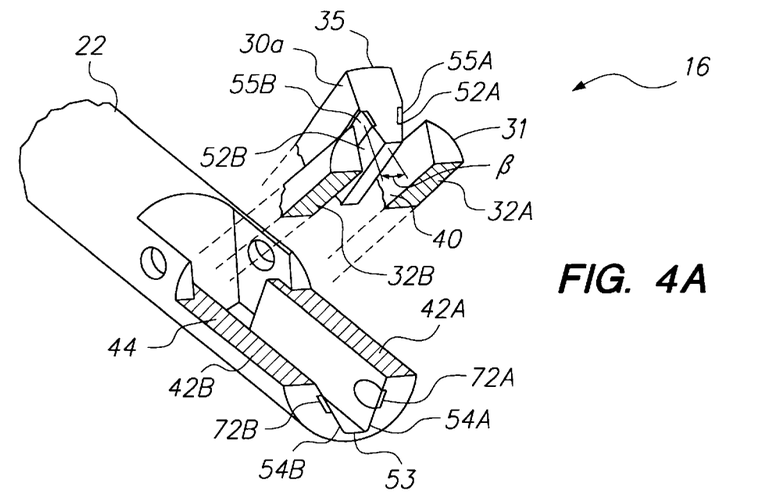
FIGS. 4A–4C are cut-away axionometric views of the working end of FIGS. 3A–3C, respectively, showing operation of the separately actuatable elements of the upper jaw subassembly.
Figures 4B, 4C:
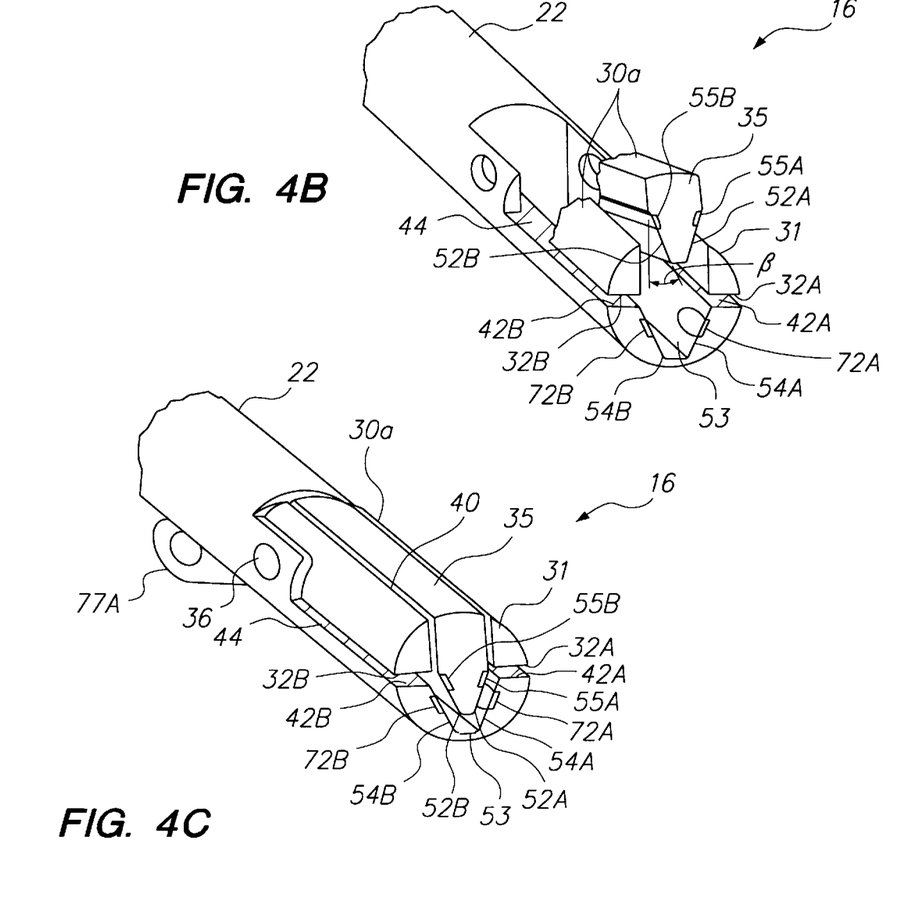

Upper jaw assembly 30a and lower jaw arm 30b are moveable to a series of positions, from a fully open position shown in FIGS. 3A and 4A, to a tissue engagement position shown in FIGS. 3B and 4B, and a fully closed position, shown in FIGS. 3C and 4C. In the embodiment of FIGS. 2–4, lower jaw arm 30b illustratively has a fixed configuration, but it should be appreciated that this jaw arm also may be movable to cooperate with upper jaw assembly 30a.

As depicted in FIG. 4A, upper jaw assembly 30a comprises perimeter jaw 31 (having right jaw face 32A and left jaw face 32B, together with an independently actuatable interior jaw arm 35. Both perimeter jaw 31 and interior jaw arm 35 of upper jaw assembly 30a rotate about pivot 36, with interior jaw arm 35 disposed for rotation within slot 41 of perimeter jaw 31. Slot 41 extends along axis 15 and is interposed between the right and left jaw faces 32A and 32B.

Lower jaw arm 30b also has cooperating right and left jaw faces 42A and 42B along its perimeter. Right and left jaw faces 32A and 32B of perimeter jaw 31 are arranged in opposing relation to right and left faces 42A and 42B, respectively, of lower jaw arm 30b, for engaging tissue therebetween. In addition, jaw faces 32A, 32B, 42A and 42B may be textured, for example, including serrations 44, to assist in gripping a vessel or tissue.

As best seen in FIGS. 4A–4C, the interior jaw arm 35 has a V-shaped cross-section having generally planar right and left surface portions 52A and 52B, respectively, that extend into V-shaped channel 53 in lower jaw arm 30b. Surface portions 52A and 52B of interior jaw arm 35 oppose similarly angled mating surfaces 54A and 54B of V-shaped channel 53. Cooperating angled surface portions 52A and 52B, and surfaces 54A and 54B, respectively, may have any suitable angle, up to and including 90°. In addition, surface portions 52A and 52B, and mating surfaces 54A and 54B, may have any suitable curved cross-section. In the embodiment illustrated in FIGS. 3 and 4, surface portions 52A and 52B are inclined at an angle β of about 60°.

In accordance with the principles of the present invention, working end 16 comprises a "double-acting" or "sequential" closing mechanism, wherein the individual components of the jaw are actuated in sequence. By the terms "double-acting" or "sequential", it is meant that upper jaw assembly 30a closes toward the lower jaw 30b in stages. In the first stage, perimeter jaw 31 moves from a fully open position (FIGS. 3A and 4A) to a tissue engaging position (FIGS. 3B and 4B), wherein the right and left jaw faces 32A and 32B of perimeter jaw 31 close against the opposing right and left jaws faces 42A and 42B of lower jaw 30b.

During the next stage, interior jaw arm 35 rotates about pivot 36 so that interior jaw arm 35 passes through slot 41 of perimeter jaw 31 (FIGS. 3C and 4C). As interior jaw arm 35 passes through slot 41, it contacts and stretches the section of tissue disposed across V-shaped channel 53 into contact with the surfaces 54A and 54B of lower jaw 30b (FIG. 4C).

With respect to FIGS. 3A–3B and 4A–4C, surface portions 52A and 52B of interior jaw arm 35 include cooperating electrodes 55A and 55B. Electrodes 55A and 55B are arranged to operate in a bi-polar mode, and may comprise any suitable material, such as gold, nickel titanium, platinum, stainless steel, aluminum or copper. RF current provided to electrodes 55A and 55B flows between the electrodes and along the length of the tissue or vessel captured in the jaw assembly.

While electrodes 55A and 55B are illustratively depicted as disposed on surface portions 52A and 52B of interior jaw arm 35, it will be appreciated that the electrodes may be disposed elsewhere, for example, on perimeter jaw 31 or lower jaw 30b, or any combination thereof. For example, the electrodes may be carried in the surfaces of perimeter jaw 31 opposing interior jaw arm 35, or on opposing surfaces 54A and 54B of V-shaped channel 53. It is sufficient for the purposes of the present invention that electrodes 55A and 55B be located where they can contact tissue engaged in the jaw structure, so that RF current can flow longitudinally through the extended tissue captured in V-shaped channel 53.

As depicted in FIGS. 3A and 4A–4C, working end 16 of the present invention also may comprise one or more sensors for measuring physiologic parameters, such as temperature or impedance. Illustrative sensors 72A and 72B are provided in a part of the jaw assembly that contacts the blood vessel section being welded, i.e., within V-shaped channel 53. Sensors 72A–72B preferably are located slightly spaced apart from electrodes 55A and 55B, and may be used to measure temperatures and/or impedance of tissue at or adjacent to the electrodes during a tissue welding operation.

Sensors 72A and 72B may comprise, for example, thermocouples or thermisters (temperature sensors that have resistances that vary with the temperature level). Thermocouples may comprise paired dissimilar metals, such as copper and constantan, which form a T-type thermocouple. Alternatively, or in addition, temperature sensors may be positioned in contact with the electrodes to measure electrode temperature.

Referring once again to FIG. 2, RF energy source 60 is coupled to electrodes 55A and 55B by wires 62A and 62B, which extend through handle 7, cable 65, and detachable coupling 66. RF energy source 60 may be a previously known, commercially available, RF generator that provides a high frequency alternating current (e.g., from 55,000 Hz to 550,000 Hz). Application of RF energy from RF energy source 60 to electrodes may be controlled using foot pedal 68 or any other suitable means, such as a switch (not shown) in handle 7. Optionally, or in addition, power controller 70 may be provided, as described in greater detail hereinbelow.

Handle portion 73 includes single lever arm 73 coupled to the jaw structure of working end 16. When single lever arm 73 is squeezed, it rotates about a pivot to cause sequential rotation of perimeter jaw 31 about pivot 36 and then rotation of interior jaw arm 35 about pivot 36. Single lever arm 73 is connected to the proximal ends of flexible reciprocating drive rods 75A and 75B.

As depicted in FIGS. 3A–3B, the distal end 74 of drive rod 75A is connected to cylindrical pin 76 in lever arm portion 77A of perimeter jaw 31. Accordingly, as single lever arm 73 is moved through the range of motion indicated at R1 in FIG. 2, perimeter jaw 31 rotates around pivot 36 and moves the jaw faces 32A and 32B of perimeter jaw 31 toward faces 42A and 42B of lower jaw 30b. Likewise, the distal end 78 of drive rod 75B connects to lever arm portion 77B of interior jaw arm 35, so that continued movement of single lever arm 73 (in the direction indicated at R2 in FIG. 2), rotates interior jaw arm 35 about its pivot until surface portions 52A–52B extend through slot 41 beyond faces 32A and 32B of perimeter jaw 31.

Simultaneous with actuation of interior jaw arm 35 relative to perimeter jaw 31, spring 79 disposed around reciprocating wire 75A within single lever arm 73 is compressed, thus allowing upper jaw assembly 30a and lower jaw arm 30b to remain in a fixed relationship. It will be appreciated that the arrangement of FIG. 2 is illustrative only, and any of a number of other mechanisms known in the art may be suitable for sequentially articulating the perimeter jaw and interior jaw arm. For example, two independent levers may be used to independently actuate the perimeter jaw and interior jaw arm. Alternatively, either or both jaws may be closed by an axially sliding cam-type mechanism known in the art.

Operation and use of the instrument of FIG. 2 in accordance with the methods of the invention is now described. While the device may be used to weld or seal blood vessels in a number of different procedures, its use is described herein in the context of performing subfacial endoscopic perforator surgery (SEPS).

In overview, the method of the present invention for welding a blood vessel includes: (1) targeting a length of a blood vessel intermediate opposing ends; (2) grasping the target vessel section at the opposing ends and maintaining the ends in a fixed relationship; (3) extending longitudinally an intermediate portion of the vessel captured between the opposing ends; and (4) delivering RF energy longitudinally through the intermediate portion in a bi-polar manner from a first electrode at one end of the vessel section to a second electrode at the other end of the vessel section.

While the science of tissue welding is not thoroughly understood, it is believed that the thermal effects on collagen molecules in excess of 75° C. to 80° C. in endothelium and vessel walls denatures and thereafter causes fusion of the collagen molecules to create a seal or weld. The duration of RF energy delivery may be determined by the surgeon's experience or visual observations of the blood vessel during the welding treatment. In an alternative embodiment described hereinafter, sensors mounted on the device measure temperature, impedance or some other parameter to determine when RF current should be discontinued.

Figure 5A:
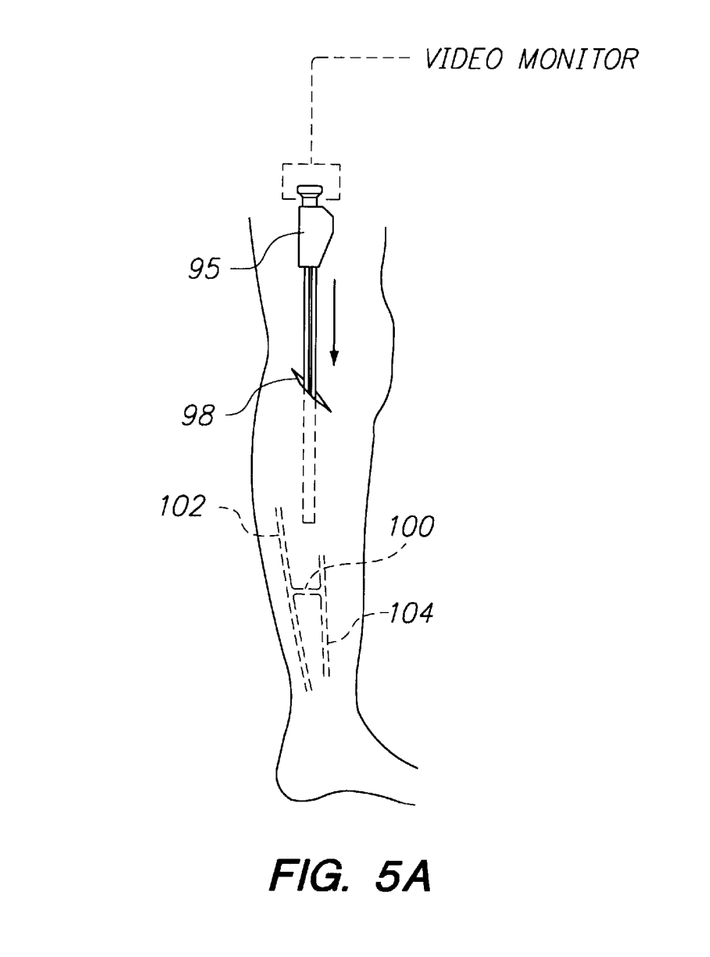
FIGS. 5A–5B are schematic views depicting use of the apparatus of FIG. 2 in a SEPS (subfacial endoscopic perforator surgery) procedure.
Figure 5B:
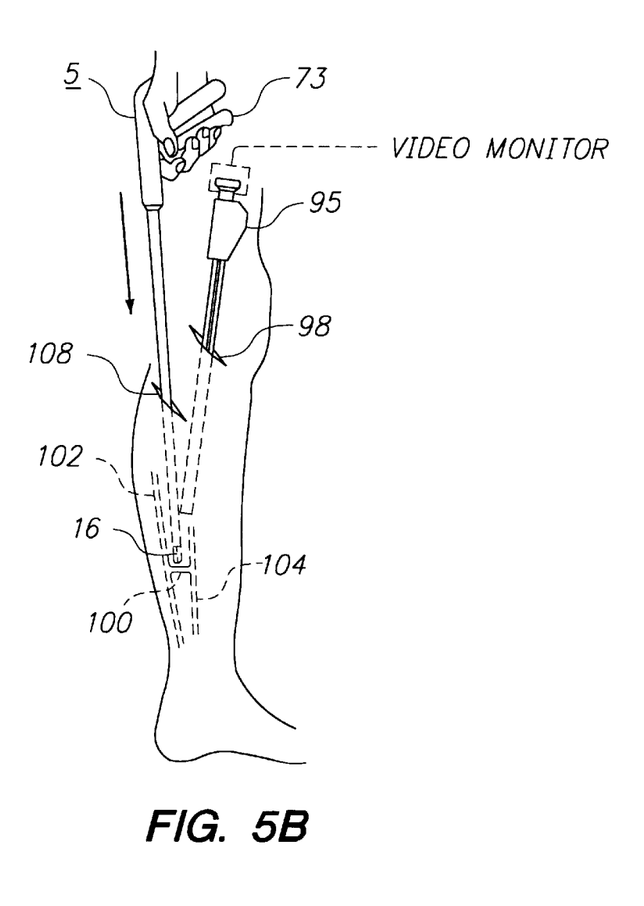

More particularly, FIG. 5A is a schematic view of a patient's leg showing a surgeon inserting endoscope 95 (or any other suitable instrument) through first incision 98 to dissect an access path to perforator 100 between vein 102 and artery 104. In FIG. 5B, the surgeon introduces the distal end of device 5 through second incision 108 toward the location of perforator 100. Alternatively, endoscope 95 and device 5 may be introduced through a single incision and a workspace around the perforator may be maintained by insufflation or mechanical retraction.

Figure 6A:
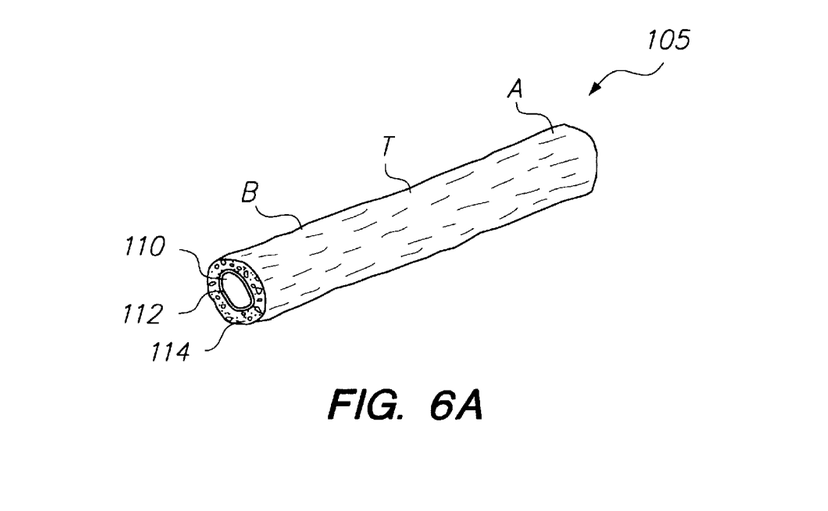
FIGS. 6A–6E are perspective views of a portion of the blood vessel targeted for treatment depicting in sequence a method of the present invention to weld or seal the blood vessel.

With respect to FIG. 6A, a particular longitudinal section 105 of perforator 100 (or any blood vessel that is selected for thermal treatment or welding in the interior of the patient's body) is described. The surgeon generally selects a central "target" portion (indicated at T) of the blood vessel section 105 for welding which is bounded by left and right ends portions A and B. The vessel has lumen 110 including endothelium 112 and vessel wall 114.

Figures 6B, 6C, 6D, 6E:
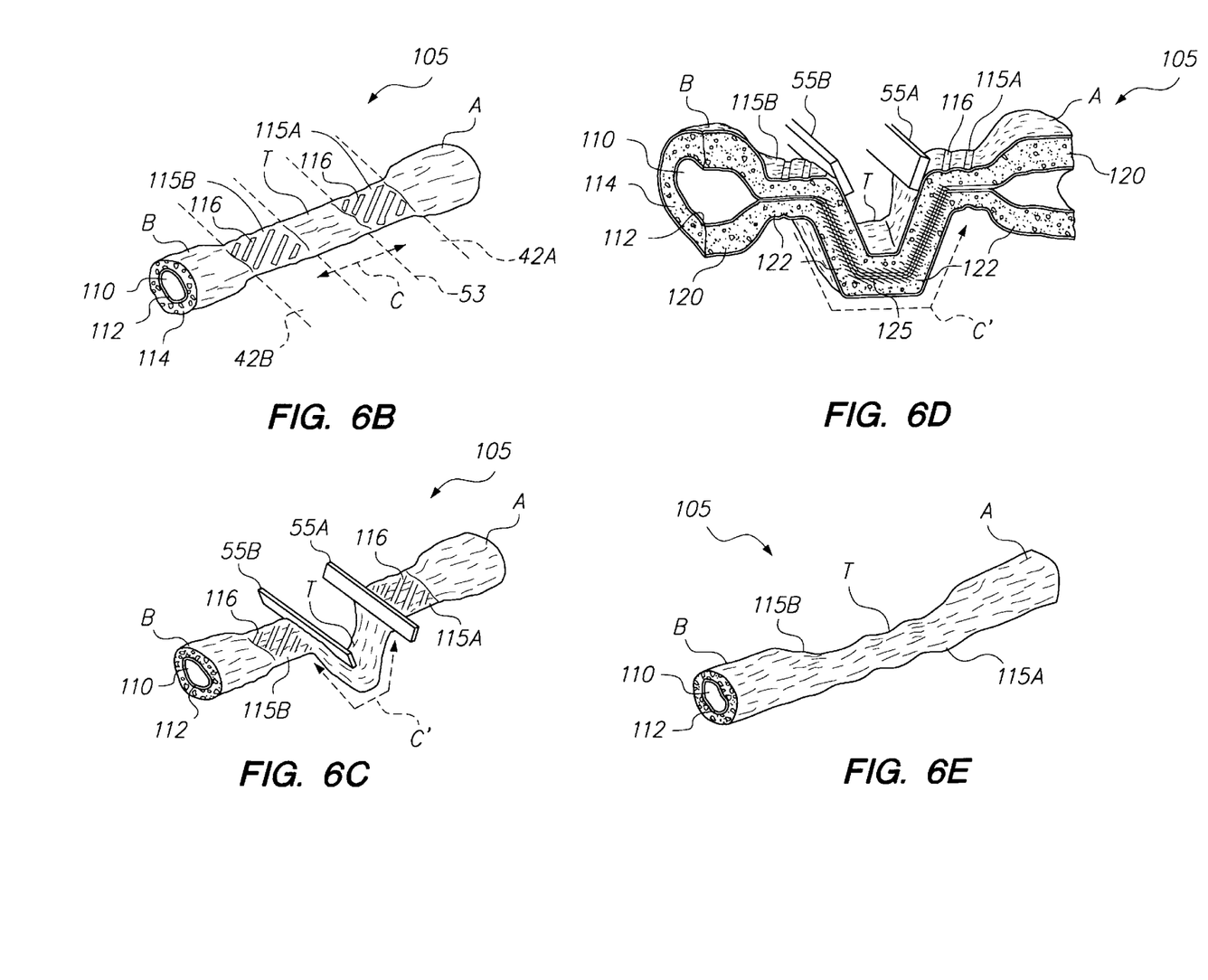

With respect to FIG. 6B, the targeted blood vessel portion is grasped and stabilized between the jaws of device 5 so that end portions A and B are captured between left and right faces 32A and 32B of perimeter jaw 31 and the opposing faces 42A and 42B, respectively, of lower jaw 30b. FIG. 6B corresponds to the jaw position shown in FIG. 4B, with end portions 115A and 115B of the vessel being flattened in the grasp of perimeter jaw 31 and lower jaw arm 30b shown in phantom view. Grip indentations 116 are caused by serrations 44 (see FIG. 4B). When blood vessel 105 is engaged with device 5, a fixed length of vessel 105, bounded by grasped portions 115A and 115B (and indicated at C in FIG. 6B), is exposed between ends A and B.

With respect to FIG. 6C the fixed length of vessel portion 105 is manipulated by actuation of interior jaw arm 35 relative to perimeter jaw 31. In particular, the closing action of interior jaw arm 35 into slot 41 and V-shaped channel 53 extends or stretches target vessel portion T beyond the plane defined by jaw faces 32A–32B and 42A–42B). FIG. 6D is an enlarged longitudinal sectional view of the blood vessel showing that target vessel section T is extended or lengthened by the actuation of interior jaw arm 35 to a length indicated at C', which is greater than initial length indicated at C.

Applicants have determined that by extending or stretching the target tissue, it is possible to alter the characteristics of target tissue to improve RF energy delivery. The extension of the target vessel portion T in FIG. 6D reduces the extracellular fluid (ECF) content of the vessel walls and endothelium that are extended by the interior jaw arm 35, thereby increasing the impedance of the target tissue to RF current flow. Without wishing to be limited to any particular theory to explain the effectiveness of the technique, it is believed that the tissue extension or manipulation has the effect of (1) decreasing the ECF content level of the target vessel section T when calculated in terms of ECF/cm$^2$ of tissue mass, and (2) making the ECF level more evenly distributed throughout the target tissue T (at the lower ECF/cm$^2$ level) whereas in the prior state, the ECF level could vary randomly within the cellular structure.

Referring to FIG. 6D, the schematic diagram depicts that the ECF in the non-extended tissue T (indicated at 120) is altered to a different state than in the extended tissue (indicated at 122). Specifically, it is believed that extracellular fluid is squeezed out of the tissue captured in V-shaped channel 53, indicated graphically by the varied patterns of cell density (compare, for example, locations 120 and 122).

An alternative way of describing the effects of the tissue manipulation caused by the extension of target portion T of vessel section 105, is that the manipulation causes the target tissue portion T to become a "fuse" or "fuse point" (as defined, for example, by decreased ECF) when subjected to the flow of RF current. A number of advantages are offered by creating a fuse-type effect in the targeted tissue.

First, the delivery of RF current between electrodes 55A and 55B delivers greater levels of thermal effects for a given current flow or intensity. Thus, target tissue may be elevated to a particular desired temperature to weld cells (or molecules) of the vessel walls and endotheluim 112 together at lower levels of RF energy delivery. Also, it may be possible to use lower levels, rather than higher levels, of RF current intensity. The lower levels of energy required for welding are expected to reduce tissue charring and smoke generation.

Second, the requisite temperature for tissue fusion can be reached more quickly, thus speeding the process of tissue welding.

Third, the bi-polar flow longitudinally through the vessel between electrodes 55A and 55B naturally welds a longer length of vessel, thereby creating a longer and more effective seal—an effect that is not possible with previously known bi-polar devices that send current "across" tissue pinched between opposing jaw-electrodes (see FIG. 1B).

Fourth, the uniformity in the ECF level in, and the resulting uniformity in thickness of, the extended target tissue allows for more uniform heating to provide a more uniform weld.

Fifth, the bi-polar current flow longitudinally through the vessel provides little or no thermal spread outwardly along the vessel in either direction, since the current only flows between the paired electrodes and not outwardly. In this respect, the higher ECF level indicated at 120 in the vessel outwardly from end portions 115A and 115B prevent outward thermal spread.

In FIG. 6C, electrodes 55A and 55A are shown in isolation (i.e., without showing other parts of upper jaw assembly 30a). To weld or seal the target vessel section T, the surgeon actuates foot pedal 68 to cause an RF current to flow between electrode 55A and electrode 55B longitudinally through the extended length C' of the vessel. Resulting elongated weld zone 125 is depicted in FIG. 6D, where the vessel walls are fused together.

In delivering RF current, a surgeon may select from a number of preset current intensity levels programmed into power controller 70 to energize the target tissue T for a time interval ranging from about 0.50 seconds to about 5.0 seconds or more, depending on current intensity level. The duration of RF energy delivery also may be determined by the surgeon's experience and by observation of the blood vessel as it is welded. FIG. 6E depicts the targeted blood vessel portion T after being welded and released from the jaw assembly of device 5.

Figure 7:
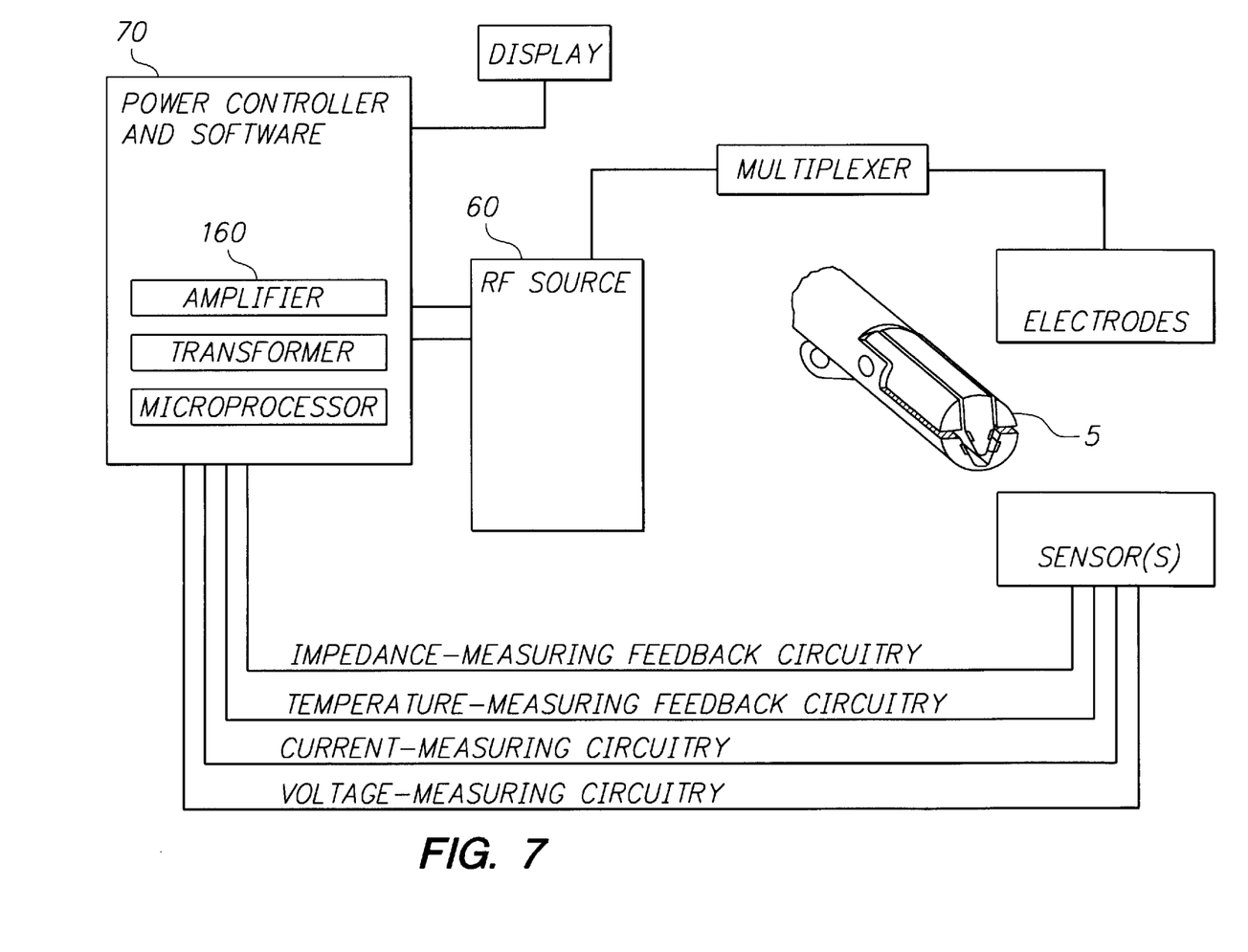
FIG. 7 is a schematic diagram of an alternative embodiment of the apparatus of the present invention.

Referring now to FIG. 7, an alternative embodiment of the apparatus and methods of the present invention is described. Device 5 is identical to device 5 of FIG. 2, the system differing only by the further inclusion of electronic power controller 70 linked to sensors 72A–72B in working end 16 of device 5. Sensors 72A and 72B are configured to monitor one or more physiologic parameters, and power controller 70 is programmed to modulate the RF energy delivery profile of the instrument responsive to the output of the sensors.

Power controller 70 controls delivery of RF power in a bi-polar manner between electrodes 55A and 55B according to predetermined parameters. Power controller 70, preferably comprises microprocessor 160 together with appropriate software, and may be programmed to deliver power according to preset parameters. Power controller 70 may include, for example, a keyboard, disk drive or other non-volatile memory system, and an operator interface as are well known in the art for operating RF electrosurgical instruments. The operator interface also may include various types of imaging systems for observing the RF treatment cycle, such as thermal sensor displays and/or impedance monitoring displays.

In a preferred manner of operation of the device for vessel welding, referred to herein as "an impedance-controlled operational mode," power controller 70 is programmed to receive signals and values for tissue impedance within the target tissue portion T (see FIGS. 6C–6D) during its operation. For example, programmed values typically may include a maximum impedance or resistance level (estimated or known) for the tissue portion targeted for welding and a minimum impedance or resistance level (also known or estimated).

The power controller 70 may include feedback circuitry or impedance measuring circuitry that measures impedance levels to control power delivery. The impedance measuring circuitry may, for example, convert current and voltage signals into an actual impedance level and signal in response to RF current flow through the target vessel portion T. A current measuring device (e.g., a transformer) and a voltage measuring device may be operatively connected to power controller 70 and the electrode pair. The power controller 70 then controls RF energy delivered to the electrodes responsive to signals generated by the impedance measuring circuitry.

For example, the controller may select a particular impedance or resistance level between the maximum and minimum impedance levels and turns off or modulates RF power delivery to the electrodes when either (i) actual measured impedance reaches the particular level, or (ii) the rate (over time) of the rise in actual impedance toward the particular selected level exceeds a parameter as it rises toward the maximum impedance level. For example, the particular impedance level, or particular rate of change, may relate to a particular level just below the maximum level or an average level between the selected maximum and minimum impedance levels.

In another manner of operation, referred to herein as "a temperature-controlled operational mode," an operator selects a target temperature level, typically a known temperature that will weld the targeted tissue. Temperature signals measured by a sensors 72A and 72B are continuously supplied to power controller 70 through feedback circuitry to control the level of power delivery to the electrodes. The power controller thus measures the difference between the actual temperature measured (or averaged) by sensors 72A and 72B and a target temperature level and thereafter select a power delivery level or delivery profile proportionate to the temperature difference at any point in time during a energy delivery cycle.

Power controller 70 further may be programmed to control power delivery based on temperature signals such that if a particular temperature is exceeded at either sensor location the power delivery will be terminated. The operator further can set a target temperature level to be maintained at a particular sensor site or averaged among several sensor sites. Power controller 70 further may include a timing device that provides the operator with the ability to maintain a particular temperature at any sensor site (or combination thereof) for a particular length of time. In addition, a power delivery profile may be programmed into controller 70 to deliver RF energy over a period of time to achieve a target temperature level or the power controller can accept a time pre-set for reaching a particular temperature level.

Alternatively, or in addition, power controller 70 also may operate in a combination temperature/impedance-controlled operational mode to still more precisely control or modulate RF power delivery which combines the above described features. All of the above-described control modes can be combined to select a preferred particular temperature (or average temperature) at one or more sensor locations in the jaw assembly such that energy delivery will be terminated if a maximum pre-set temperature is reached.

The impedance control also may be incorporated as previously described to modulate or control power delivery based on impedance levels to achieve a particular sensed temperature or temperature profile. Thus, the temperature at the sensor array can be maintained at a pre-set temperature based on impedance feedback unless a maximum temperature is exceeded, at which energy delivery is modulated or terminated.

Power controller 70 preferably includes circuitry for measuring actual power output delivery, which is indicated by an actual power output signal. In another manner of operation or "power-controlled operational mode," an operator selects a target actual power delivery for treating tissue, which typically is a level of actual power known or estimated to achieve a certain temperature in the target tissue which can be measured in joules delivered. A time profile may be programmed into power controller 70 to deliver a predetermined amount of power over a particular period of time to achieve a target energy delivery (and temperature) in tissue. Thus, in a power-controlled operational mode, the power controller 70 may deliver RF energy at or along a continuous range of pre-set power levels or according to a pre-set power delivery profile (RF power delivery over a period of time). Any of these pre-sets can be indicated by a power level delivery signal or power profile signal.

The power controller 70 and software together with the above described feedback circuitry thus are capable of full process monitoring and continuous control of the following operational variables: (i) power delivery; (ii) time, temperature and impedance parameters of a selected energy delivery cycle; (iii) vectoring RF current delivery in different directions between the electrodes via a multiplexer, and (iv) mono-polar or bi-polar energy delivery, since in some circumstances it may be desirable to use mono-polar energy delivery.

In addition, power controller 70 besides vectoring RF current between the electrodes may be employed to monitor circuit continuity for each electrode. Specifically, microprocessor 160 may sequentially receive and store digital data representing impedance and temperature values and the temperature and impedance values also may be displayed on the operator interface as numerical values. The temperature and impedance values may be compared by microprocessor 160 with pre-programmed temperature and impedance limits as described above and when the measured temperature value or impedance value at a particular site exceeds a pre-determined limit, a warning or other indication can be given on the operator interface (such as a warning light) while at the same time the delivery of energy to a particular electrode site can be decreased. Calculated surface temperatures of the vessel also may be forwarded by controller 70 to the display and compared to a predetermined limit to activate a warning indicator on the display.

It should be appreciated that the present invention is specially adapted to weld blood vessels. The device of the present invention may further include a reciprocating blade member carried in an axial slot (not shown) for transecting the welded blood vessel. Alternatively, a separate scissors-type blade that is rotatable within a slot in interior jaw arm 35 (not shown) may be provided for transecting the welded blood vessel.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. Apparatus for welding a blood vessel comprising:
    a first member having a first blood vessel engaging surface and a portion defining a first opening extending through the first blood vessel engaging surface;
    a second member having a second blood vessel engaging surface and a portion defining a second opening extending through the second blood vessel engaging surface, the second opening aligned with the first opening, the second member operatively coupled to the first member to grasp the blood vessel to define an engagement plane;
    an extension member movable from a retracted position, wherein the extension member is remote from the engagement plane, to an extended position, wherein the extension member passes through the first and second openings and the engagement plane, the extension member adapted to contact and extend a portion of the blood vessel when moved to the extended position; and
    a first electrode disposed to apply RF energy to the portion of the blood vessel when the extension member is in the extended position.

2. The apparatus of claim 1 wherein the first opening communicates with a slot in the first member and the second opening communicates with a channel formed in the second member.

3. The apparatus of claim 2 wherein the channel forms a mating surface to a surface of the extension member.

4. The apparatus of claim 1 wherein the first member and second members comprise first and second opposing jaw arms.

5. The apparatus of claim 1 further comprising an actuation mechanism for moving at least one of the first and second opposing jaw arms towards and away from other.

6. The apparatus of claim 1 wherein the extension member is independently operable from the first and second members.

7. The apparatus of claim 1 wherein the first electrode is disposed on a first surface of the extension member, the apparatus further comprising a second electrode disposed on a second surface of the extension member.

8. The apparatus of claim 1 further comprising a sensor disposed on one of the first member, the second member and extension member.

9. The apparatus of claim 8 wherein the sensor is a temperature sensor, the apparatus further comprising an RF power controller that modulates the RF energy responsive to an output of the temperature sensor.

10. The apparatus of claim 8 wherein the sensor is an impedance-monitoring sensor, the apparatus further comprising an RF power controller that modulates the RF energy responsive to an output of the impedance-monitoring sensor.

11. A method for welding a blood vessel comprising:
    identifying a blood vessel for welding, the blood vessel having first and second ends;
    grasping the blood vessel at the first and second ends;
    longitudinally extending an intermediate portion of the blood vessel located between the first and second ends to alter an impedance of the intermediate portion while maintaining the ends in a fixed relationship relative to one another;
    applying RF energy through the intermediate portion of the blood vessel so that an RF current flows longitudinally along the intermediate portion and welds the intermediate portion.

12. The method of claim 11 wherein longitudinally extending an intermediate portion of the blood vessel further comprises reducing an extracellular fluid content of the blood vessel.

13. The method of claim 11 wherein longitudinally extending an intermediate portion of the blood vessel further comprises reducing the intermediate portion to a substantially uniform thickness.

14. The method of claim 11 wherein longitudinally extending an intermediate portion of the blood vessel to alter an impedance of the intermediate portion further comprises making the impedance of the intermediate portion substantially uniform.

15. The method of claim 11 further comprising contacting a sensor to the intermediate portion of the blood vessel.

16. The method of claim 15 wherein the sensor monitors temperature of the intermediate portion of the blood vessel and generates an output signal, the method further comprising modulating the RF energy applied to the intermediate portion responsive to the output signal.

17. The method of claim 16 further comprising modulating the RF energy applied to the intermediate portion to prevent a preselected temperature value from being exceeded.

18. The method of claim 15 wherein the sensor monitors impedance of the intermediate portion of the blood vessel and generates an output signal, the method further comprising modulating the RF energy applied to the intermediate portion responsive to the output signal.

19. The method of claim 18 further comprising modulating the RF energy applied to the intermediate portion to prevent a preselected impedance value from being exceeded.

20. The method of claim 11 further comprising monitoring a value of RF energy delivered to the intermediate portion and ceasing application of RF energy responsive the value exceeding a predetermined value.

21. Apparatus for welding a blood vessel comprising:
a first member having a first blood vessel engaging surface and a portion defining a first opening extending through the first blood vessel engaging surface;
a second member having a second blood vessel engaging surface and a portion defining a second opening extending through the second blood vessel engaging surface, the second opening aligned with the first opening, the second member operatively coupled to the first member to grasp the blood vessel to define an engagement plane;
an extension member having an atraumatic surface, and movable from a retracted position, wherein the atraumatic surface is remote from the engagement plane, to an extended position, wherein the atraumatic surface passes through the first and second openings and the engagement plane, the atraumatic surface adapted to contact and longitudinally extend a portion of the blood vessel, without cutting, when moved to the extended position; and
a first electrode disposed to apply RF energy to the portion of the blood vessel when the extension member is in the extended position.

22. The apparatus of claim 21 wherein the first opening communicates with a slot in the first member and the second opening communicates with a channel formed in the second member.

23. The apparatus of claim 22 wherein the channel forms a mating surface to a surface of the extension member.

24. The apparatus of claim 21 wherein the first and second members comprise first and second opposing jaw arms.

25. The apparatus of claim 21 further comprising an actuation mechanist for moving at least one of the first and second opposing jaw arms towards and away from other.

26. The apparatus of claim 21 wherein the extension member is independently operable from the first and second members.

27. The apparatus of claim 21 wherein the first electrode is disposed on a first surface of the extension member, the apparatus further comprising a second electrode disposed on a second surface of the extension member.

28. The apparatus of claim 21 further comprising a sensor disposed on one of the first member, the second member and extension member.

29. The apparatus of claim 28 wherein the sensor is a temperature sensor, the apparatus further comprising an RF power controller that modulates the RF energy responsive to an output of the temperature sensor.

30. The apparatus of claim 28 wherein the sensor is an impedance-monitoring sensor, the apparatus further comprising an RF power controller that modulates the RF energy responsive to an output of the impedance-monitoring sensor.

31. A method for welding a blood vessel comprising:
identifying a blood vessel for welding, the blood vessel having first and second ends;
grasping the blood vessel at the first and second ends;
contacting an extension member having an atraumatic surface to an intermediate portion of the blood vessel between the first and second ends;
longitudinally extending the intermediate portion of the blood vessel to alter an impedance of the intermediate portion while maintaining the ends in a fixed relationship relative to one another;
applying RF energy through the intermediate portion of the blood vessel so that an RF current flows longitudinally along the intermediate portion and welds the intermediate portion.

32. The method of claim 31 wherein longitudinally extending an intermediate portion of the blood vessel further comprises reducing an extracellular fluid content of the blood vessel.

33. The method of claim 31 wherein longitudinally extending an intermediate portion of the blood vessel further comprises reducing the intermediate portion to a substantially uniform thickness.

34. The method of claim 31 wherein longitudinally extending an intermediate portion of the blood vessel to alter an impedance of the intermediate portion further comprises making the impedance of the intermediate portion substantially uniform.

35. The method of claim 31 further comprising contacting a sensor to the intermediate portion of the blood vessel.

36. The method of claim 35 wherein the sensor monitors temperature of the intermediate portion of the blood vessel and generates an output signal, the method further comprising modulating the RF energy applied to the intermediate portion responsive to the output signal.

37. The method of claim 36 further comprising modulating the RF energy applied to the intermediate portion to prevent a preselected temperature value from being exceeded.

38. The method of claim 35 wherein the sensor monitors impedance of the intermediate portion of the blood vessel and generates an output signal, the method further comprising modulating the RF energy applied to the intermediate portion responsive to the output signal.

39. The method of claim 38 further comprising modulating the RF energy applied to the intermediate portion to prevent a preselected impedance value from being exceeded.

40. The method of claim 31 further comprising monitoring a value of RF energy delivered to the intermediate portion and ceasing application of RF energy responsive the value exceeding a predetermined value.

* * * * *